(12) United States Patent
Egger (10) Patent No.: US 7,141,007 B2
(45) Date of Patent: Nov. 28, 2006

(54) APPARATUS FOR PHYSICAL TRAINING OF PERSONS

(76) Inventor: Norbert Egger, Eschenbachgasse 4a, A-5020, Salzburg (AT)

( * ) Notice: Subject to any disclaimer, the term of this patent is extended or adjusted under 35 U.S.C. 154(b) by 876 days.

(21) Appl. No.: 09/818,999

(22) Filed: Mar. 28, 2001

(65) Prior Publication Data

US 2002/0025889 A1    Feb. 28, 2002

Related U.S. Application Data

(63) Continuation-in-part of application No. 09/164,361, filed on Oct. 1, 1998, now abandoned.

(51) Int. Cl.
  *A63B 22/06* (2006.01)
(52) U.S. Cl. ............................. 482/57; 601/9
(58) Field of Classification Search ............ 482/57–60, 482/63; 601/23, 33–36, 41, 6, 9–11; 128/898
  See application file for complete search history.

(56) References Cited

U.S. PATENT DOCUMENTS

| 72,631 | A | * | 12/1867 | Hadfield | 601/11 |
| 1,336,774 | A | * | 4/1920 | Cooper | 4/528 |
| 2,138,527 | A | * | 11/1938 | Newman | 417/25 |
| 4,421,109 | A | * | 12/1983 | Thornton | 601/35 |
| 5,133,339 | A | * | 7/1992 | Whalen et al. | 601/23 |
| 5,514,079 | A | * | 5/1996 | Dillon | 601/151 |
| 6,539,946 | B1 | * | 4/2003 | Weyergans | 128/898 |

FOREIGN PATENT DOCUMENTS

| AU | 400305 | 12/1995 |
| CH | 675971 | 11/1990 |
| EP | 0906774 | 9/1998 |
| FR | 1163577 | 9/1958 |
| FR | 2618342 | 1/1989 |
| FR | 2789893 | 8/2000 |
| RU | 2006218 | 1/1994 |
| RU | 2061515 | 6/1996 |
| RU | 2071619 | 1/1997 |
| RU | 2113829 | 6/1998 |

OTHER PUBLICATIONS

Patent Abstracts of Japan, entitled "Pressure-Reduced Training Facility" of Fujiyama Yuji, vol. 1996, No. 9, Sep. 30, 1996 of JP 08 112373, May 7, 1996.

* cited by examiner

*Primary Examiner*—Jerome Donnelly
*Assistant Examiner*—Tam Nguyen
(74) *Attorney, Agent, or Firm*—Dykema Gossett PLLC (57) ABSTRACT

The present invention relates to an apparatus for increasing blood flow to the skin of a person using the apparatus for regeneration of skin and digestion of adipose cells without causing an increase of gravity effects on the person. The apparatus comprises a work-out device to be actuated with the legs, which is enclosed by an air-tight housing. The housing in the waist area encloses the person. The apparatus further comprises a device for the production of a differential pressure in said housing, which is arranged so as to alternatingly produce a pressure reduction and a pressure increase in the housing. Within said housing, a support means is arranged to take the body weight off the legs of the person and to enable to separately control the effects of adipose cell digestion due to low pressure stimulation and the effects on the cardiovascular system by the work-out device.

28 Claims, 8 Drawing Sheets

APPARATUS FOR PHYSICAL TRAINING OF PERSONS

CROSS REFERENCE TO RELATED APPLICATION

This is a continuation-in-part of application Ser. No. 09/164,361, filed Oct. 1, 1998, now abandoned the priority of which is hereby claimed.

FIELD OF THE INVENTION

The present invention relates to an apparatus for physical training of persons that includes a work-out device to be actuated with the legs.

BACKGROUND OF THE INVENTION

An apparatus of this kind is for instance known from EP 0 906 774. Different exercises can be performed and therapeutical concepts can be realized by means of the known apparatus. The vacuum that acts on the lower body half of the person during operation of the apparatus has a stimulating effect, wherein in particular the blood circulation of the skin is supported. Thus, an aimed reduction of the body tissue can for instance be achieved. The therapeutical effect can be adapted to the respective needs by adjusting the vacuum, possibly also by a temporarily applied overpressure, by the physical load of the person through the working apparatus and by the air conditioning of the chamber. The therapeutical effects is achieved through the reduced pressure in the chamber acting on the skin tissue.

Although the known apparatus supplies favorable results and can be used in a plurality of indications, the need for an ever more selective application possibility arose.

A training apparatus comprising a treadmill is known from U.S. Pat. No. 5,133,339, which is in particular determined for the use in zero gravity. Since the vacuum in the apparatus determines the effective weight of the person onto the treadmill, the limits especially in the range of low specific load are tight. The apparatus can be used for training and for rehabilitation, since an exercise of the muscoskeletal tissue is possible in this case so that a growth of the muscular and bone mass is enhanced. The U.S. Pat. No. 5,133,339 relies solely on the training effect which is achieved by standing up or walking in the low-pressure chamber: Without standing up or walking, the gravity effect on the legs cannot be simulated. The device of U.S. Pat. No. 5,122,339 is disadvantageous, because it puts too much strain on the lower joints. It is rather a training apparatus than an apparatus for slimming.

Furthermore, a large number of fitness devices are known which can be used for the physical training of persons. In the large majority of the fitness devices that are used the training person exerts a certain force against the resistance of the device or actuates certain movable components. These devices, however, are solely designed for use under ambient conditions.

It is further known to simulate a training at high altitudes in that the test person is enclosed in a chamber in which there is overall a reduced pressure or at least a reduced partial pressure of oxygen. Moreover, from U.S. Pat. No. 4,944,506 and from WO-91/01162 training apparatuses are known in which the test person is located partly under water.

It is the object of the present invention to further develop the aforementioned apparatuses in order to achieve an improved slimming effect without putting too much strain on the legs.

It is also the object of the present invention to develop the above-mentioned apparatus in a manner that a possibly far reaching adaptation to specially elaborated therapeutic concepts or training programs is possible.

It is another object to provide a better method for the slimming of persons which will not put too much strain on the body.

SUMMARY OF THE INVENTION

The above objects are achieved in accordance with the invention in that the work-out device is enclosed by an air-tight housing having an opening which is formed for the tight enclosure of the person in the area of the waist or below the same, and that a device for producing a differential pressure is arranged in the housing or is connected with the same. This differential pressure can principally concern either a pressure below or above atmospheric.

It has suprisingly been found that a considerably improved training effect can be achieved by subjecting large areas of the body of the training person to a pressure below atmospheric. This effect makes it possible that the physical exercise may be reduced without any drawbacks on the slimming effect. However, there is a negative effect of the low pressure on the breathing function if the pressure below atmospheric encompasses also the thorax. It is best to subject the person to a pressure below atmospheric from the waist down. It is assumed that the apparatus in accordance with the invention is based on a similar effective mechanism as the treatment by cupping, which is largely used in Chinese medicine. It is most beneficial if the sealing occurs in the waist region of the person. In principle it is also possible to provide a sealing below the waist, e.g. on the legs, so that only these are subject to the pressure below atmospheric.

The pressure range in which the work-out takes place with the device according to the invention correspond substantially to ambient conditions as they occur naturally in various regions of the world. A reduction of the pressure by 0.1 bar over ambient conditions has proved to be most beneficial. A reduction of 0.2 bar would currently be regarded as a useful upper limit. The endurableness of the pressure below atmospheric also depends on the speed of the lowering of the pressure. A slower reduction improves the endurableness of the test person.

It is assumed that the special efficacy of the apparatus in accordance with the invention is based on the fact that by the uneven distribution of the pressure over the body surface there is a shifting of the tissue liquids in the body. This increases both the blood flow as well as the lymph liquid in the outer skin and in the subcutaneous fatty tissue in the respective skin sections. As a result of the simultaneously performed movement the lymph liquid is conveyed off and the skin is simultaneously repeatedly supplied with nutritive blood. In the end this causes a regenerative impulse for the skin tissue, which subsequently also leads to a digestion of the adipose cells. In this way there is an improvement for the figure in addition to the training effect. A particularly advantageous aspect is that this effect occurs in the critical regions of the lower abdomen, the hips and the thighs.

In this way the present invention differs substantially from the known forms of the so-called hypoxy training, which simulates training at high altitudes. In such a form of training the blood improves its absorbing capacity for oxygen, which in the end leads to an improvement in the performance in stamina area. However, as in such a form of training and treatment the reduced pressure acts evenly over the entire body including the lungs, the effects of the present invention cannot be achieved.

In an alternative embodiment of the invention a pressure increase is performed during the work-out of the person instead of a pressure reduction. In this way blood and tissue liquids are conversely transferred from the legs into the upper part of the body and enriched there more strongly with oxygen and nutrients. Following a pressure balance these bodily fluids return to the lower part of the body, which causes the aforementioned regenerative impulse. It is theoretically possible to change over once or several times during a training unit from pressure below atmospheric to pressure above atmospheric and vice-versa. This helps to achieve a particularly intensive exchange of the matter and liquid within the body.

The apparatus of the present invention cannot only be used as a mere training device, but also as a medical device, e.g. as an ergometer with which the physical powers of a person can be determined.

The above objects are also achieved by an apparatus for the slimming of persons that comprises a housing in which a working device operable by the legs and a seat for supporting the body of the person are arranged, an opening in the housing said opening surrounding the person's body, a sealing collar for sealing the housing in the area of the opening against the person's body, and a vacuum pump for generating a vacuum in the housing. Moreover, the invention comprises a method of physical training of persons.

This object is achieved according to the invention in that at least one further chamber is provided in the area of the opening, which is sealed against the person by means of a further sealing collar and whose internal pressure can be adjusted independent of the internal pressure in the first chamber.

The vacuum in the chamber exerts a local and a systemic effect on the person operating the working unit in the apparatus. The extent of the systemic effect is, however, different in the area of the extremities compared to the area of the trunk. Moreover, the local conditions, such as the build-up of fatty tissue, are different. By the adjust of differing pressure levels this fact can be optimally taken into account. It is especially favorable that the pressure conditioning during the duration of an exercising unit may have a differing temporal course so that a plurality of parameters may be optimized independent from one another.

Furthermore, it turned out to be favorable that the first sealing collar is provided for sealing the area of the person's hip, whereas the second sealing collar is provided for sealing the area of the person's thorax. The second sealing collar will preferably be pulled up to the area below the person's axillae. Thus, the abdominal portion and a large part of the thorax can be influenced separately.

For a simple transport and the set-up in a fitness studio, which are often not very spacious, the apparatus shall, in an advantageous design, be formed especially compact. This object is solved according to the invention in that the housing is formed as a round body, in particular in the shape of an egg.

The design of the housing as a round body on the one hand provides an especially compact structural shape, and at the same time the round body reveals the best properties to contain a pressure above or below atmospheric. In this configuration, a high stability is obtained even if the wall thickness is relatively thin. The use of thin wall thicknesses also has an advantageous effect on the manufacturing costs and the weight of the apparatus.

It turned out to be especially advantageous that the housing can be divided into half shells, wherein each half shell comprises a part of the opening that are joined by means of a locking system. The divisibility of thee apparatus enables the easy transport of the apparatus also for instance through narrow door openings. A quick acting locking system enables a quick disassembly and assembly of the apparatus.

At the same time, the form of the apparatus in two halves, each of which comprising a part of the opening, enables a simple entering the apparatus, since the two parts can for instance by moved apart for entering the apparatus.

Furthermore, it turned out to be advantageous if a portion of the housing at the opening is formed as a door element. This enables a very simple entering and exiting of the apparatus. It is conceivable to form the door element as an element that can be folded downwards and to arrange stair elements on the side folded down in order to further facilitate the entry.

The person preferably sits in the housing, so that the working muscles in the legs are not subjected to the body weight but can be exercised with only a light loading of the joints in the leg.

According to a preferred embodiment it is provided that the seat can be adjusted in height to support the person. This adjustment in height enables to position the person, if needed, deeper in the apparatus, e.g. for treating abdominal and hip problems, or higher, e.g. if only the legs and the buttock is to be treated.

According to another preferred embodiment, the opening is arranged on the side, and a lounger means extends through the opening into the housing, wherein the person lies during the physical exercise. The lying position relieves the buttock from the body weight and enables training with minimum stress on the joints. At the same time, the lying position considerable releases the stress on the cardiovascular system and allows for the blood in the legs to easily circulate although the skin tissue is subjected to low pressure. This effect is enhanced the higher the legs are lifted above the body.

It may be advantageous if the lounger means is longitudinally displaceable within the housing. Thereby, the training is enabled in various positions. On the one hand, an aimed effect on the legs and the buttock and on the other hand on the abdomen and the hips may be realized.

It turned out to be favorable if the seat is arranged on the lounger. The seat prevents a slipping into the vacuum chamber caused by the suction force of the vacuum.

Furthermore, supporting means for the shoulders of the person are arranged on the lounger. The shoulder support protects the person from slipping out during the overpressure phase or when the position is lowered.

It turned out to be favorable if the sealing collar is formed as an inflatable sealing ring and seals the opening against the lounger means and the person. An inflatable seal ring optimally adapts to the respective person and seals the opening in particular also between the opening and the lounger.

The sealing collar is preferably formed as a vacuum cover. Vacuum covers of that type exist in various sizes so that it can easily be adapted to the size or figures of the respective person, i.e. abdominal, waist or hip diameter. The vacuum cover is taken on by the person outside the apparatus and is then pulled onto a sealing ring of the opening.

It is especially favorable if the working means is formed as a stepper, a room bicycle or an ellipse trainer. These working devices can be operated in sitting and lying position. The seat in the embodiment as a stepper serves for supporting the body so that a high pressure does not have to be exerted onto the legs. In case of an embodiment as an ellipse trainer, the legs are relieved from the body weight and only the suction force acts onto the legs.

In a further embodiment it is provided that the working means is driven by an electromotor and is braked by the body power of the person.

This also enables a passive operation in which an especially precise adjustment of the load of the person can be performed.

Moreover, it may be provided that a control means is arranged outside the housing. In this manner, the apparatus can easily be operated by the person or by assisting persons. Via a terminal having operating units and at least one display connected to the control means, the training person may call and have displayed all values of the current operating condition of the apparatus according to the invention as well as physiologic values, e.g. the pressure, the treading frequency, the work done and to be done, heart rate, blood pressure. Moreover, the training person may program the exercise conditions via the terminal. In order to obtain a favorable accessibility of the terminal, this terminal is arranged on a movable arm.

According to a further embodiment, it turned out to be favorable if the housing contains at least one additional pressure chamber which may have a pressure different to that in the main chamber. The additional chamber may be arranged in the area of the trunk, in particular in the area of the abdomen of the person. Thus, it is possible to exert a different pressure onto different body parts. The second chamber may already be arranged within the housing or it may be applied to the person outside the housing. For instance the second chamber enables an overpressure effect onto the abdomen, whereas the legs are exposed to a vacuum effect, or vice versa.

Another embodiment provides that magnetic coils are arranged in at least one chamber to generate a magnetic field in the area of the person. The magnetic coils may for instance encompass the abdomen or the legs of the person. In this manner, magnetic fields for supporting the therapeutical effect can be used.

Furthermore, it is advantageous if light sources for irradiating persons are provided in at least one chamber. Rays of different wave lengths, including infrared and ultraviolet rays, can be supplied via optical fibers. The irradiation can be directed in an aimed manner onto certain body regions.

An essential influence can furthermore be achieved in that an air conditioning means for adjusting the temperature and the air moisture is provided. The selectivity of the application is increased in that the air conditioning means may air condition each individual chamber independent from the other chamber.

Furthermore, a first vacuum pump for evacuating the main chamber and a vacuum pump for each further chamber may be provided. In this manner the largest possible independence when controlling the vacuum is achieved.

An inexpensive alternative of this embodiment can be achieved in that one single vacuum pump exists which is connected to each individual chamber via separate pressure control valve.

Furthermore, the invention provides a method for physical exercise by means of an apparatus, comprising a housing in which a working means operable by the legs and a seat for supporting the person's body is arranged, an opening in the housing, said opening surrounding the person's body, a sealing collar for sealing the housing in the area of the opening against the person's body, and a vacuum pump for generating a vacuum in the housing, wherein first of all a treading motion is exerted onto the working means and then the switch-on of the vacuum pump are activated offset in time.

Furthermore, it may be provided that the lowering of the pressure is adapted to the circulatory system of the person. For this purpose, a device is integrated into the apparatus according to the invention, which besides the pulse rate also measures the blood pressure and/or the respiratory rate and/or the heart rate of the training person and which outputs this in the form of signals. In a further development of the invention, these measuring devices may be connected to the control unit in a data-transmitting manner, said control unit controlling the exercise in accordance with the measured physical load values. In an automatic control it has proven to be especially favorable to underlie the pulse rate or the heart rate. For this purpose, the training person may for instance wear a pulse belt etc. which is connected to the control means and which determines the training program on the basis of the data received.

It also turned out to be advantageous when the vacuum is lowered at predetermined intervals in predetermined time intervals.

Furthermore, it is advantageous when after reaching a predetermined maximum vacuum, a permanent switching over between the normal pressure and the vacuum in predetermined time intervals is generated.

It is advantageous when the treading resistance and/or the vacuum are controlled in accordance with the pulse rate of the person.

Furthermore, the treading resistance and the interval switching may be coupled with one another.

It becomes clear from the above-mentioned facts that the method consists of an adaptation of treading resistance, treading motion and vacuum effect by constantly taking the person's pulse rate into consideration.

At the beginning of the slimming procedure, only a treading motion takes place, while normal pressure prevails in the housing. After the beginning of the treading motion, the pump is switched on and a vacuum is generated. In this manner it is prevented that a vacuum effect takes place without a treading motion, since otherwise the blood is drawn into the legs because of the vacuum, but it is not returned sufficiently by the action of the muscles. This effect could lead to an insufficient supply of blood in the brain and to unconsciousness. Therefore, the slimming device according to the invention is equipped with a monitoring means is provided, which monitors the treading motion and which interrupts the power supply to the vacuum pump or opens one or a plurality of valves in the vacuum portion when a treading motion is interrupted for a predetermined period of time.

The treading resistance is preferably adapted to the respective person and is adjusted specially. When treating problem parts of the body in the area of the thighs, the treading resistance is for instance set to 0.8 to a maximum of 1.2 Watts per kilogram body weight. In this case, the seat position in the housing is set to the high position. When treating problem parts in the area of the hip, the treading resistance is set to at least 1 to a maximum of 2 Watts per kilogram body weight. In this case, the person takes a deep seat position so that the abdomen and the hips are subjected to the vacuum effect.

In order to obtain an optimal effect, a regular treading motion is required. 50 to 70 revolutions per minute turned out to be especially suitable.

As already described, the first minutes are tread without the effect of the vacuum in order to stimulate the circulatory system. This first phase takes about 3 minutes. Then, the atmospheric pressure in the apparatus is lowered to 10 millibar and is then lowered every 4 to 5 minutes by further 5 to 10 millibar. The lowering of the pressure as well as the time intervals are adapted to the circulatory system of the person. In case of persons have a stable circulatory system, the vacuum is raised between 30 and a maximum of 50 millibar, in case of persons having a weak circulatory system, the range is 20 to 25 millibar.

If a vacuum of 20 millibar is reached, the interval switching starts. During this interval switching, a permanent change between lowered pressure and normal pressure takes place in the apparatus. An increased pressure instead of a normal pressure could also be exerted.

The intervals are adapted to the respective person and are usually within a period of 10 to 90 seconds sucking followed by 10 to 30 seconds ventilation and 10 to 90 seconds overpressure, respectively.

The interval switching can also be coupled with the treading resistance. While the vacuum acts on the person the treading resistance is increased. If the housing is ventilated, the treading resistance reduces. The reversed coupling can be chosen according to the respective person's need.

Since the vacuum represents a load of the circulatory system, the treading resistance and the vacuum must be reduced when the pulse rate is too high.

BRIEF DESCRIPTION OF THE DRAWINGS

The invention is now explained in closer detail by reference to the embodiments shown in the drawings. In the figures.

DETAILED DESCRIPTION OF THE PREFERRED EMBODIMENTS

Figure 1:
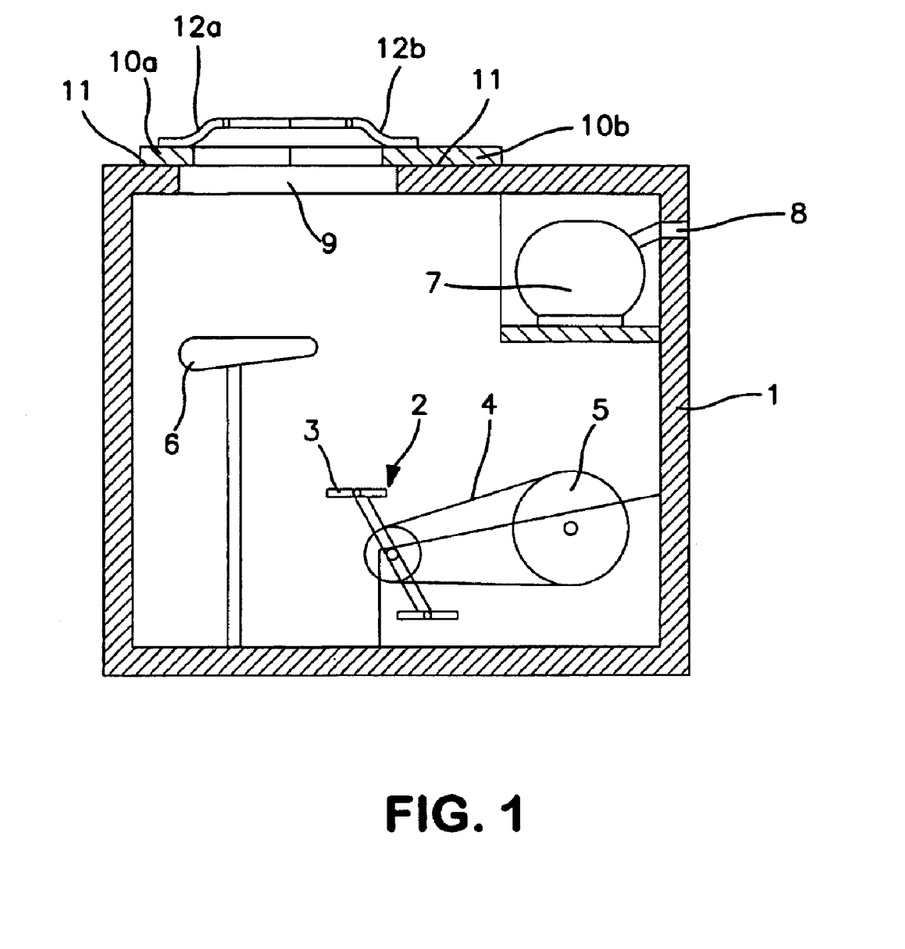
FIG. 1 shows a first embodiment of the apparatus in accordance with the invention in a sectional view.
Figure 2:
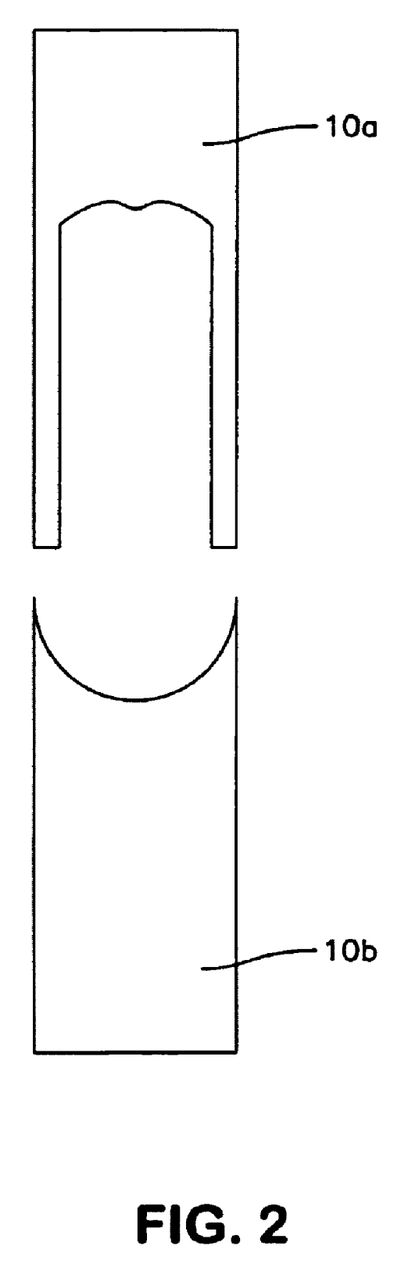
FIG. 2 shows sealing elements in a top view and FIG. 3 shows a further embodiment of the invention in a sectional view pursuant to FIG. 1.

The apparatus pursuant to FIG. 1 consists substantially of a housing 1 of an air-tight design in which an exercise bicycle 2 is arranged consisting of pedals 3, a drive belt 4 and a flywheel 5 which is braked by a braking apparatus not shown in detail. A seat 6 is provided for the person actuating the apparatus. The flywheel 5 and braking apparatus provides a resistance to the treading motion of the legs of the user. Moreover, a vacuum pump 7 is arranged in the housing, which pump discharges air from the interior of the housing 1 through an opening 8 to the outside. An opening 9 is arranged in the upper zone of the housing 1 for tight enclosure of a user's waist area, the opening being defined by two displaceable lid portions 10a, and 10b which are sealed off with respect to the housing 1 by means of seals 11 and sealing elements 12a, 12b on the upper side of the lid portions 10a and 10b which are made up of rubber so as to sealingly enclose the waist of the person actuating the apparatus. The lid portions 10a, 10b are pushed apart in order to allow the entry into the apparatus from above. Alternatively, there can also be arranged an entrance opening on the side or the housing may be entirely arranged in two parts in order to allow a particularly simple entry into the apparatus. Thereafter, all openings are closed in order to ensure an air-tight occlusion of the inner chamber of the housing 1 from the outside environment. The sealing elements 12a, 12b should enclose the test person's waist as tightly as possible. Thereafter a predetermined pressure below atmospheric is produced in the interior of the housing 1 by means of the vacuum pump 7.

It is obvious for the man skilled in the art that this pressure below atmospheric is regulated accordingly and is adjustable according to the respective needs.

In an alternative embodiment, it may not only be provided that air is sucked off via the vacuum pump 7, but that also in a well-defined manner air is supplied from the ambient environment in order to produce predetermined climatic conditions such as temperature, humidity and the like in the interior of housing 1. This is not shown in the present figures.

Figure 3:
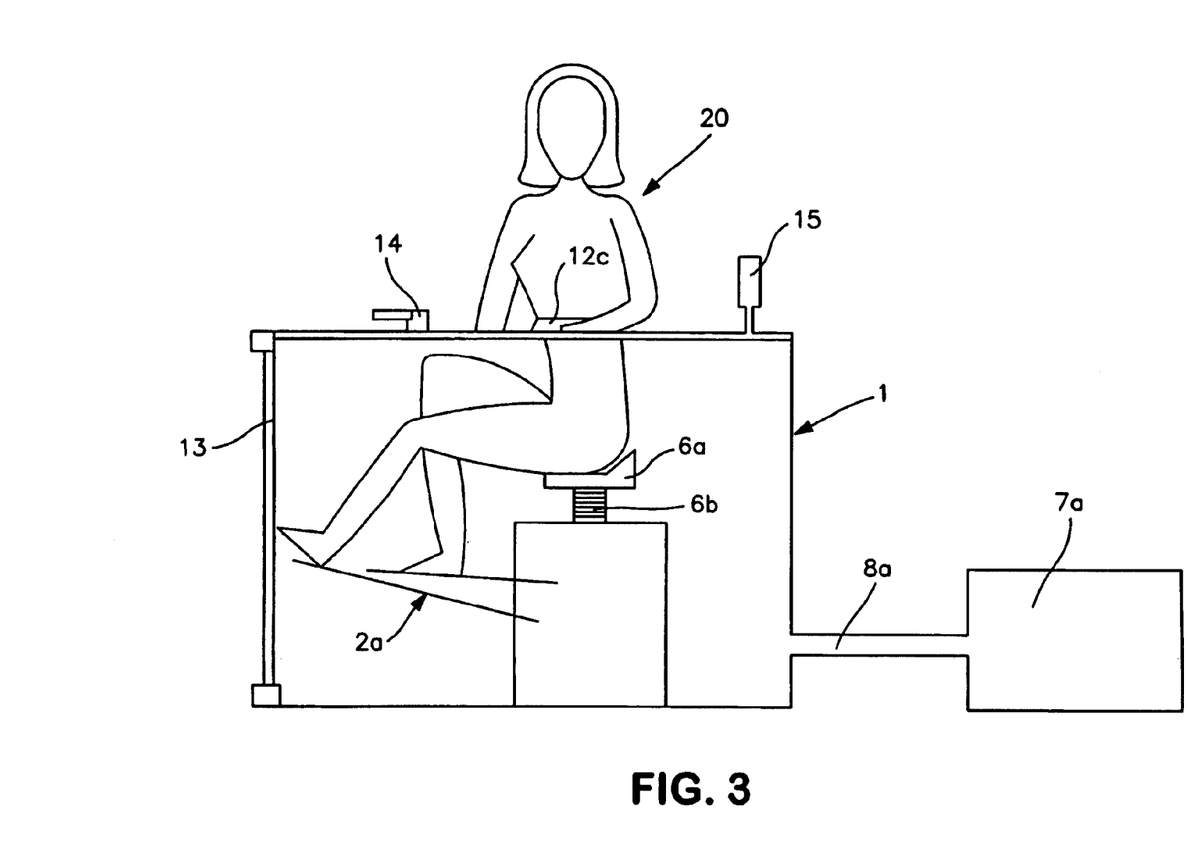

The embodiment of FIG. 3 is distinguished from the embodiment of FIG. 1 in that a pump 7a is arrange outside of box 1 and is connected with the same via a line 8a. This allows reducing the operating noise of the apparatus. The pump is provided with a design that allows changing over so as to produce both a pressure below atmospheric and a pressure above atmospheric in box 1.

A stepper 2a is arranged in box 1, which stepper is actuated by the indicated test person 20. An air valve 14 and a barometric measuring device 15 for the pressure within the box are provided on the upper side of the box. A door 13 is arranged at the front side of the box 1 for entering the apparatus. The seat 6a is vertically adjustable via rotation of threaded support 6b, and the waist of a person using the apparatus is surrounded by a sealing (closure) means 12c.

Figure 4:
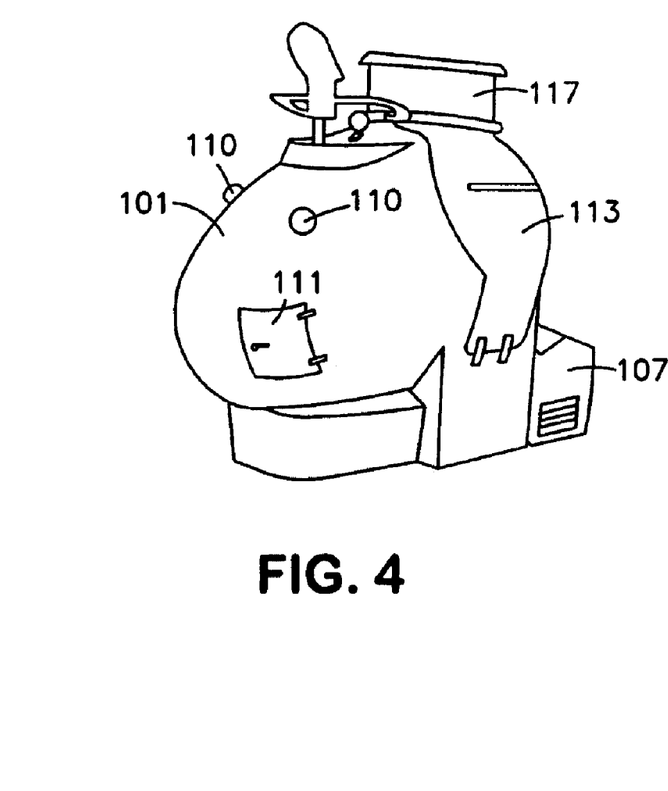
FIG. 4 diagrammatically shows an axonometric view of an apparatus according to the invention for use while sitting.
Figure 5:
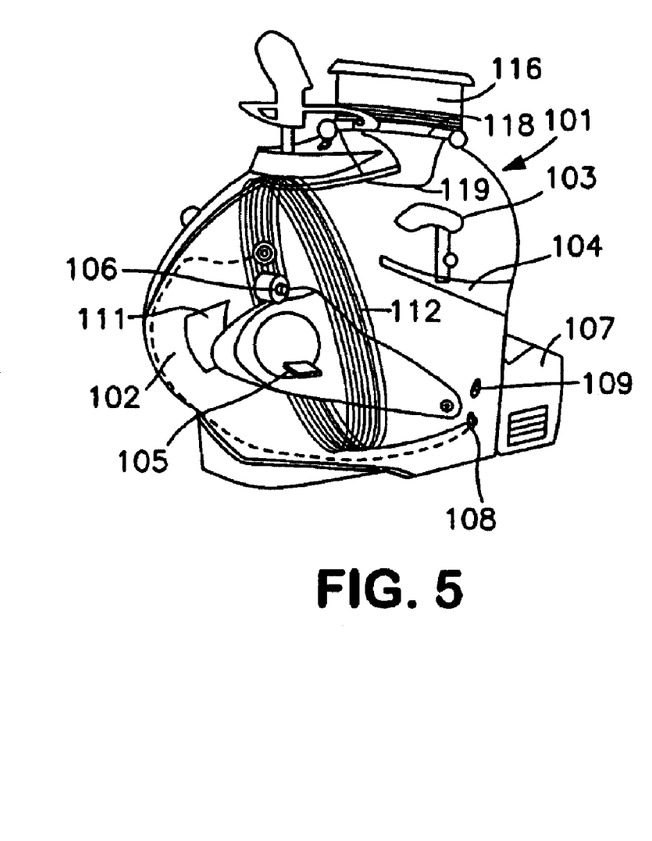
FIG. 5 shows the apparatus shown in FIG. 4 in a partially cut view.
Figure 6:
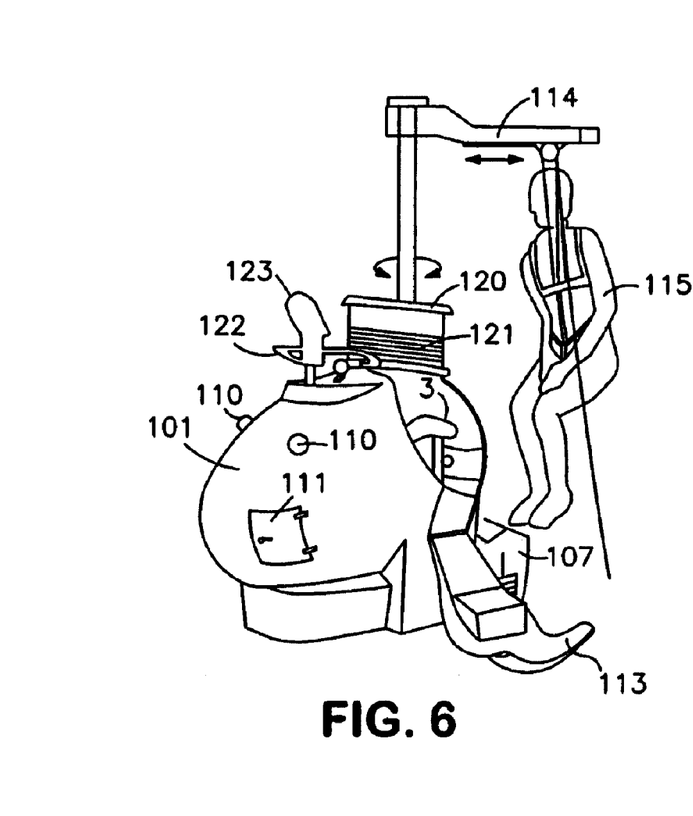
FIG. 6 shows the apparatus shown in FIG. 4 with a additional means for entry help.

The apparatus as shown in FIGS. 4–6 comprises a housing 101 encompassing a main chamber 102 in which a seat 103 is arranged on a shifting rail 104. Furthermore, a working means in the form of a room bicycle 105 is arranged in the main chamber 102, the room bicycle being drivable by an electromotor 106. Operating openings 111 that can be locked in an air-tight manner for instance enable to attach the legs of a person, that is handicapped in moving, from the outside to the pedals of the room bicycle 105.

A box 107 is connected to the chamber 102, which includes a vacuum pump—not shown in detail—and a control means for controlling the additional functions that will now be described.

Air can be sucked off via an opening 108 in order to generate a vacuum. A further opening 109 serves for air conditioning, i.e. in particular for cooling the main chamber 102 and for adjusting the air moisture.

Light sources 110 serve for irradiating the legs of the person using the apparatus. Magnetic coils 112 are provided for building up a therapeutically advantageous magnetic field in the area of the person's legs.

An entry door 113 opening towards the bottom enables an easy access into the apparatus. The entry door 113 is arranged in the area of the opening 108. In the unfolded state it may be provided that the entry door in the area visible in the unfolded condition has elevations that may be used by the person using the apparatus as a stairway, which enables an easier entry.

As may in particular be seen from FIG. 6, it is possible to lift disables persons by means of an entry help in the form of a crane 114 into the apparatus. In this case the person is indicated by reference numeral 115.

A further chamber 116 is arranged above the main chamber 102, said further chamber being formed by a cylindrical extension 117. An opening 118 is formed in the area of the transition of the housing 101 to the extension 117, said opening having a sealing collar 119 through which the chamber 102 is sealed against the person 115 in the area of the hip. The sealing collar 119 can be provided in the form of panties having two openings for the person's legs.

A further sealing collar 120 serves for sealing the further chamber 116 against the body in the upper portion of the thorax. A further magnetic coil 121 is provided to generate a magnetic field in the thorax area. The further chamber 116 cannot only be loaded by pressure separate from the main chamber 102, but it can also be ventilated separately and has its own light sources.

Handles 122 serve for supporting the person and for accommodating a display unit 123.

Figure 7:
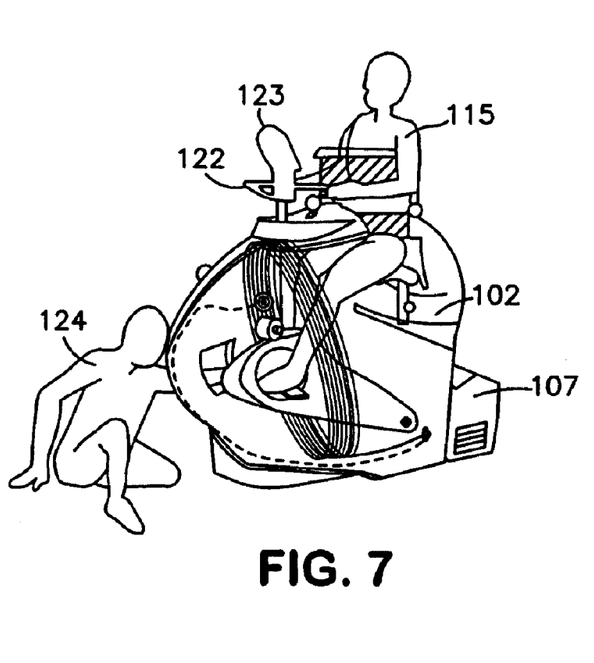
FIG. 7 shows a sketch for operating the apparatus shown in FIGS. 4 to 6, FIGS. 8 and 9 show two alternative circuit diagrams for carrying out the invention.

In FIG. 7 a person 124 is shown, who attaches the legs of a person 115 at the working means 105 through operating openings. In particular in case of disabled people, it may prove to be especially advantageous if the working means is provided with foot attachments so that the feet are held at the working means.

Figure 8:
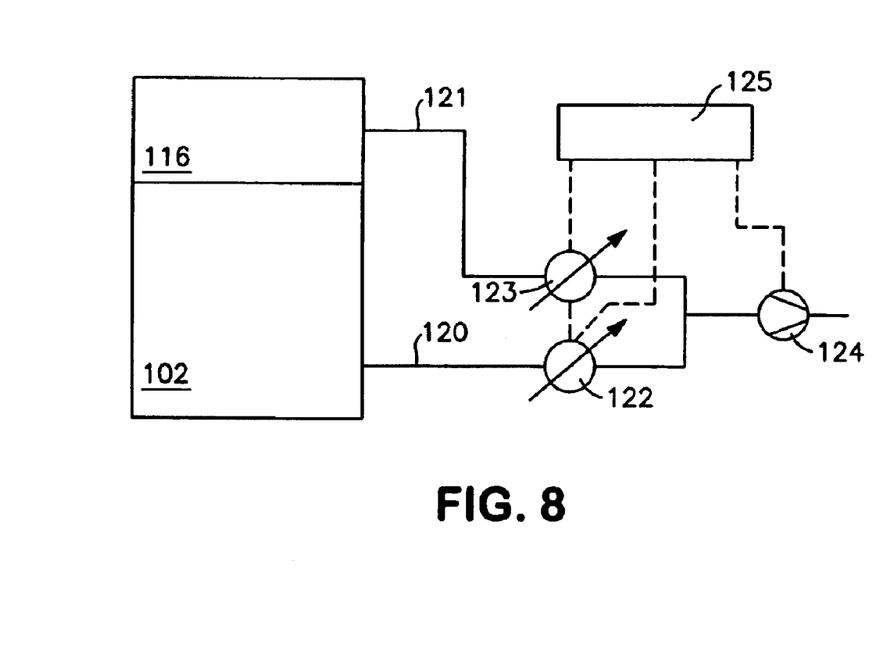

As shown in FIG. 8, a first line 120 leads out of the main chamber 102 and a second line 121 leads from the further chamber 116 to a first or second pressure control valve 122, 123. A vacuum pump 124 is arranged at the downstream side of the pressure control valves 122, 123 to evacuate the chambers 102 and 116. A control means 125 controls the pressure control valves 122, 123 and the vacuum pump 124. In this manner, the respective desired pressure is set in the chambers 102 and 116.

Figure 9:
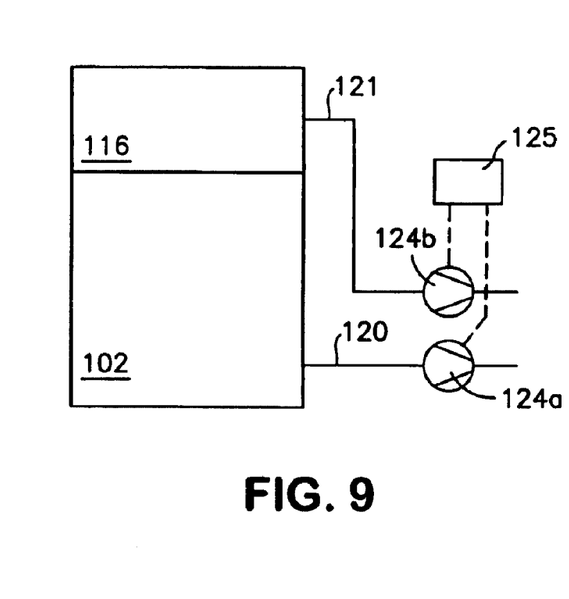

The embodiment shown in FIG. 9 differs from that shown in FIG. 8 in that an independent vacuum pump 124a and 124b is provided for each chamber 102 and 116, the vacuum pumps being separately driveable by the control means 125.

A further embodiment of the invention is shown in FIGS. 10 to 14. The apparatus shown in these Figures is a training apparatus that is to be used by the respective person in a lying position.

In the description of the drawings the same components are designated by the same reference numerals as in FIG. 4 to 9.

Figure 10:
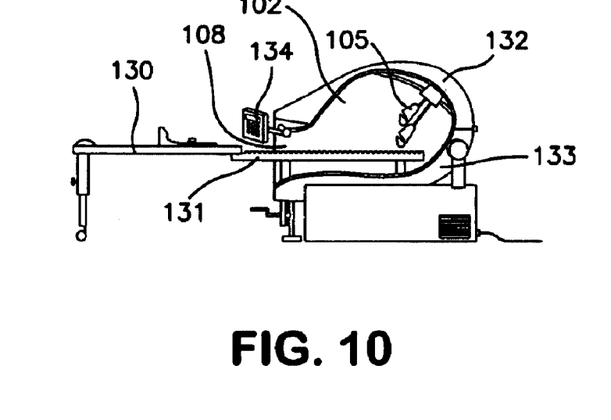
FIG. 10 shows a diagrammatic view of a further apparatus according to the invention for use in lying position in a sectional view.

The apparatus shown in FIG. 10 consists of a housing 101 which encompasses a main chamber 102. A working means in the form of a room bicycle 105 is arranged within this main chamber 102. The housing 101 is arranged in such a manner that the opening 108 is located at the side of the housing so that the opening encompasses the person using the apparatus in a lying position. A lounger means 130 extends into the housing through the opening 108. The lounger means 130 can be moved to different positions within the housing via a frame 131 having a lock element arranged within the housing and extending through the opening 108 out of the housing 101 and which engages the lower side of the lounger means 130. This configuration allows an adaptation of the area of the body that is exposed to the pressure. If the lounger is placed in the leftmost position in FIG. 10, the pressure acts only on the legs and the buttock; if the lounger is placed in the rightmost position, the pressure, in addition to acting on the legs, acts also on the abdomen and the hips. The work-out device 105 is supported by supporting means that allow an ergonometric adjustment to the person irrespective of the position of the lounger. Thus, the position of the lounger may be adjusted independently of the body proportions of the person using the device.

A seat 103 is arranged on the lounger 130, which is formed as lock, element and which in case of use is located between the legs of the person. In order to take the different body sizes of the training persons into account, the seat is preferably displaceably arranged on the lounger. The seat on the lounger prevents the person from being pulled into the housing during the vacuum phase.

Figures 11, 12, 13:
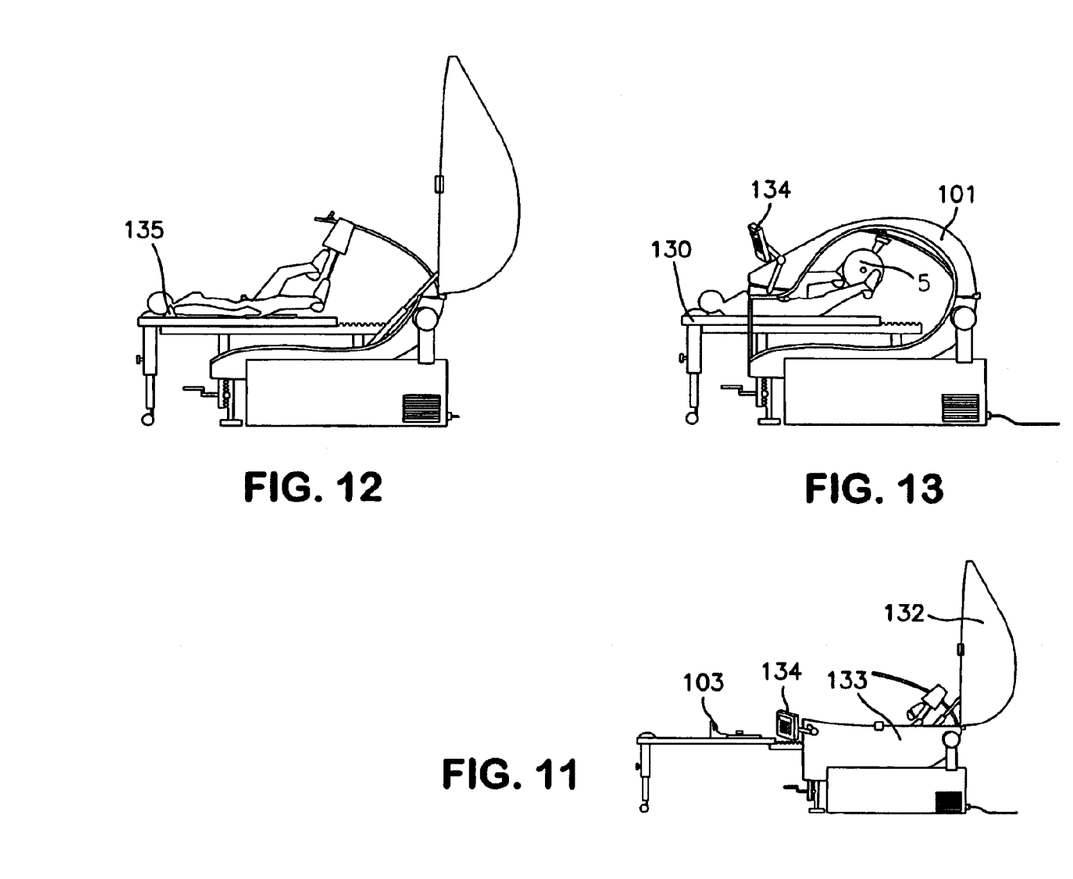
FIG. 11 shows the apparatus shown in FIG. 10 in folded condition.
FIG. 12 shows the apparatus shown in FIG. 10, wherein a person is lying in the apparatus.
FIG. 13 shows the apparatus shown in FIG. 12 in folded condition.

In order to enable an easier entry, the device, as shown in FIG. 11, may easily be unfolded into two half shells, wherein the two half shell elements 132 and 133 are separated from one another in the area of the opening 108.

FIG. 12 shows the apparatus when used. In this view, a person is lying on the lounger 130, and the lounger 130 has been adjusted to the desired position within the housing. The person is, as already mentioned, on the one hand supported by the seat 103. The person is further secured by supports 135 on the lounger 130, wherein the supports are arranged above the shoulder of the person to be treated. These supports are in particular necessary when the lounger is tilted from the horizontal position into another position, as for instance shown in FIG. 14. During cycles of high pressure, the shoulder supports keeps the person from being pushed out of the apparatus. The lounger is configured in such a way that it can be brought into any tilted position up to the vertical position during exercise.

The shoulder supports 135 and the seat 103 from support means for the body of the person using the apparatus. These supports means maintain the body in the selected common relative to the work-out means 5.

Figure 14:
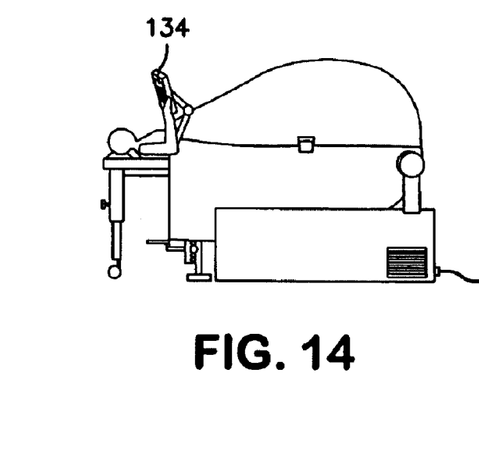
FIG. 14 shows the apparatus shown in FIG. 10 to 13 in inclined condition.

A control unit 134 is arranged outside the housing, and can either be operated by the training person itself or by an assisting person. For this purpose, the control unit 134 is provided with an arm-like folding mechanism to move it into different positions. In FIG. 14, it is also seen that, due to the jointed arm-like mechanism the person in the device can place the terminal 134 in such a manner that it is easily accessible.

To seal the person against the opening and against the lounger, it may be provided that the person puts out an inflatable inner ring outside the housing, said ring being put on in the non-inflated condition, and which is inflated after taking the final position on the lounger. It is also possible that the person puts on a vacuum cover, which takes the sealing role.

It is especially advantageous if various seals cooperate to realize a complete sealing of the lounger 130 against the opening 108 and the person against the lounger 130 and the opening 108. In this case, the area between the lower side of the lounger means 130 and the portions of the opening 108 encompassing same can be sealed by a separate sealing means.

Figure 15:
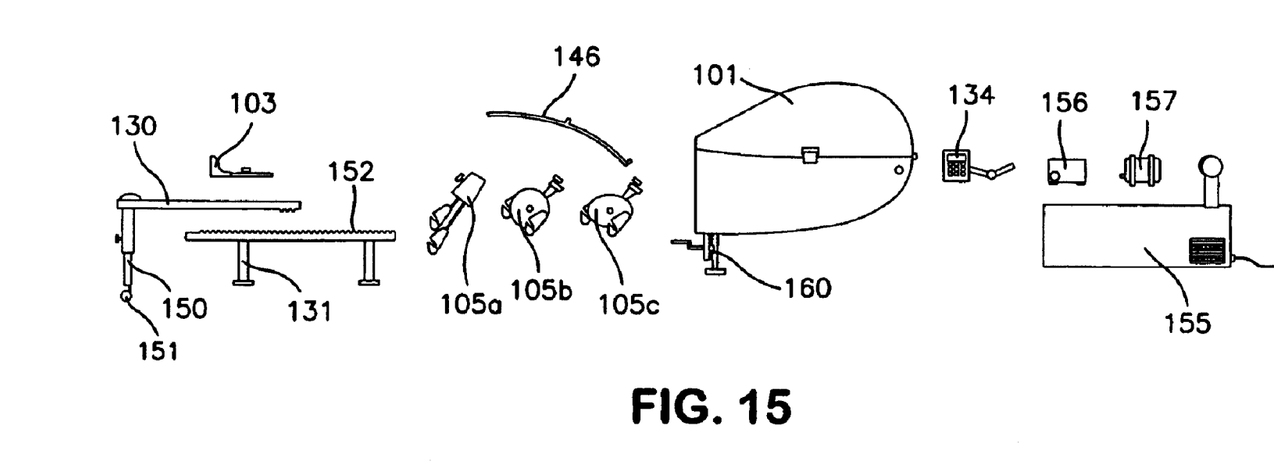
FIG. 15 shows the apparatus shown in FIG. 10 to 14 in an exploded view.

The modular structure of the apparatus of FIGS. 10 to 14 can be derived from FIG. 15. The modular structure enables a fast and flexible adaptation to various training situations. The modular structure allows also easy transport and easy maintenance.

The training apparatus includes as a first module the adjustable lounger device comprising the lounger or rest 130 and the frame 131 as well as the shoulder support 135 and the seat 103. The seat and the shoulder support are longitudinally displaceably arranged on the lounger 130. The frame 131 is substantially stationary, whereas the lounger 130 on which the body rests during training is movable with respect to the frame 131, and, as stated above, can be adjusted in height, length and inclination and can be easily removed for cleaning purposes. For adjustment, the lounger comprises adjustable feet 150 having rollers 151. On its upper side, the frame is provided with latches 152, which engage into corresponding counter-latches of the lounger 130 and which fix it in a certain longitudinal position.

Interchangeable working devices 105*a*, 105*b*, 105*c* are provided as a second module, which can all be operated in lying position. FIG. 15 shows a stepper 105*a*, a bicycle trainer 105*b* and an ellipsoidal trainer 105*c*. The working devices 105*a–c* are displaceably supported at an adjustment means in the form of a rail 146. The working devices 105*a–c* all comprise data and signal transmission means which can be connected to the control means. Moreover, the working devices 105*a–c* may optionally provided with an electromotor.

A further module is the control means or the terminal 134, respectively.

The supply unit 155 is a further module. The devices for the air conditioning control, e.g. an air conditioning system 156, as well as a pump 157 for generating a vacuum or overpressure in the chamber 102 are stored in the supply unit. The supply unit 155 consists of a housing, which has a sound encapsulation so that as few noise as possible is generated during operation in rehabilitation or fitness centers.

The housing forms the last module, which is structured as stated above. The housing 101 rests on a frame 160 adjustable in height that is anchored on the ground.

Due to the modular structure, the apparatus of FIGS. 10 to 14 can be converted from a device for training in lying position into a device for training in sitting position as shown in FIGS. 4 to 7 by exchanging only a small number of elements. Also, the modular structure allows for the manufacturer to tailor the apparatus exactly to the needs of a costumer.

In an embodiment that is especially advantageous in this respect, the housing is designed in a manner that it can be used for training in lying and in sitting position. For this purpose the opening must merely turned upwards after the lounger was removed and replaced by a seat.

The apparatus shown in FIG. 10 to 15 can, as well as the device shown in to FIGS. 4 to 9, be equipped with additionally integrated magnetic coils, air conditioning means or light irradiation means.

In the apparatus, overpressure as well as a vacuum can be regularly or steplike raised or lowered over a predetermined period of time. In the various phases of treatment, an interval circuit switches the overpressure or vacuum in different periods of time on or off, respectively. Overpressure and vacuum may change with one another in one phase of treatment. Overpressure and vacuum may be controlled manually and automatically. Regarding the automatic control, it may be provided that this control is calculated on the basis of the heart rate or the blood pressure of the person to be treated, or on the basis of the temperature behavior in the vacuum chamber or at the surface of the skin of the training person or on the basis of the resistance of the ergometer.

The present invention enables to realize an training and a therapy adapted in an improved way to the particularities of the respective person.

I claim:

1. An apparatus for increasing blood flow to a person's skin for regeneration of skin and digestion of adipose cells the person inherently having a body weight and, the apparatus comprising a work-out device to be actuated with the person's legs, said work-out device being enclosed by an air-tight housing, said housing comprising an opening which is formed for a tight enclosure of the person's waist area, with a pressure device for producing differential pressure in said housing, said pressure device being connected with said housing and being arranged so as to alternatingly produce a pressure reduction and a pressure increase in the housing, and a support means in the housing for supporting the person and taking the person's body weight off the person's legs.

2. An apparatus according to claim 1, wherein the support means is a seat.

3. An apparatus according to claim 1, wherein the device for producing a differential pressure is arranged so as to ensure a predetermined air pressure throughout the housing.

4. An apparatus according to claim 1, wherein the pressure device provides a reduction in pressure from 0.02 bar to 0.2 bar.

5. An apparatus according to claim 1, wherein the pressure device provides a reduction in pressure from 0.05 bar to 0.15 bar.

6. An apparatus according to claim 2, wherein the seat is adjustable in height.

7. Apparatus for increasing blood flow to a person's skin for regeneration of skin and digestion of adipose cells, the apparatus comprising:

means for doing physical exercise, said means being actuated by the person's legs;

means for generating a pressure different from ambient pressure;

means for containing the pressure generated by said means for generating a pressure, said means for containing the pressure being arranged such that it houses the means for doing physical exercise and that it sealingly surrounds lower parts of said person's body;

wherein said apparatus further comprises means for supporting said person's body weight, said means for supporting the body weight of said person being arranged such that the person's legs are not exposed to the body weight during use of said means for doing physical exercise.

8. A method for increasing blood flow to a person's skin and regeneration of skin and digestion of adipose cells, comprising the following steps:
  placing a person on a support means in a pressure chamber such that the person from the waist down is enclosed in the chamber, said pressure chamber being equipped with a work-out means and containing a pressure;
  closing seals around said person to contain the pressure in said pressure chamber;
  having said person use the work-out means against a resistance generated by the work-out means without exposing the person's legs to said person's body weight;
  wherein said method comprises the further steps of
  first stimulating the circulatory system of said person by using the workout device under ambient conditions,
  then generating a pressure below atmospheric after said person has been using the work-out means for a specific amount of time.

9. An apparatus for increasing blood flow to a person's skin, for regeneration of skin and digestion of adipose cells, the apparatus comprising a work-out device to be actuated with the person's legs; an air-tight housing enclosing the work-out device, said housing comprising an opening which is formed for tight enclosure of the person in a waist area; a device for producing a differential pressure in said housing, said device being connected with said housing and being arranged so as to alternatingly produce a pressure reduction and a pressure increase; and a support means within said housing for removing body weight from the legs of the person while actuating the work-out device, said support means being a seat.

10. An apparatus for increasing blood flow to a user's skin for regeneration of skin and digestion of adipose cells, the apparatus comprising a work-out device to be actuated with the user's legs, said work out device being enclosed by an air-tight housing, said housing comprising an opening which is formed for a tight enclosure of the user's waist area, with a device for producing differential pressure in said housing, said device being connected with said housing and being arranged so as to alternatingly produce a pressure reduction and a pressure increase in the housing, wherein within said housing, a support means is arranged to take the user's body weight off said legs, and wherein a permanent interval switching between low pressure and increased pressure in said housing takes place if a low pressure limit is reached, said low pressure limit being between 0.02 bar and 0.05 bar.

11. An apparatus according to claim 10, wherein the support means is a seat.

12. An apparatus according to claim 11, wherein the seat is adjustable in height.

13. An apparatus according to claim 10, wherein the device for producing a differential pressure is arranged so as to ensure a predetermined pressure throughout the housing.

14. An apparatus for increasing blood flow to a user's skin for regeneration of skin and digestion of adipose cells, the apparatus comprising a work-out device to be actuated with a user's legs, said work-out device being enclosed by an air-tight housing, said housing comprising an opening which is formed for a tight enclosure of the user's waist area, with a device for producing differential pressure in said housing, said device being connected with said housing and being arranged so as to alternatingly produce a pressure reduction and a pressure increase in the housing, wherein within said housing, a support means is arranged to take the user's body weight off said legs, and wherein the apparatus is adapted to perform a continuous change between low pressure and increased pressure within a period of 10 to 90 seconds.

15. An apparatus according to claim 14, wherein the device for producing a differential pressure is arranged so as to ensure a predetermined pressure throughout the housing.

16. An apparatus according to claim 14, wherein the pressure device provides a reduction in pressure from 0.02 bar to 0.05 bar.

17. An apparatus for increasing blood flow to a user's skin for regeneration of skin and digestion of adipose cells, the apparatus comprising a work-out device to be actuated with the user's legs, said work-out device being enclosed by an air-tight housing, said housing comprising an opening which is formed for a tight enclosure of the user's waist area, with a device for producing a differential pressure in said housing, said device being connected with said housing and being arranged so as to alternatingly produce a pressure reduction and a pressure increase in the housing, wherein within said housing a support means is arranged to take the user's body weight off said legs, wherein said work-out device is adapted to generate a treading resistance, wherein an interval switching between low pressure and increased pressure takes place and wherein said treading resistance is coupled to said interval switching such that the treading resistance increases while said low pressure acts on said user.

18. An apparatus according to claim 17, wherein the device for producing a differential pressure is arranged so as to ensure a predetermined pressure throughout the housing.

19. An apparatus according to claim 17, wherein the pressure device provides a reduction in pressure from 0.02 bar to 0.05 bar.

20. An apparatus for increasing blood flow to a user's skin for regeneration of skin and digestion of adipose cells, the apparatus comprising a work-out device to be actuated with the user's legs, said work-out device being enclosed by an air-tight housing, said housing comprising an opening which is formed for a tight enclosure of the user's waist area, with a device for producing differential pressure in said housing, said device being connected with said housing and being arranged so as to alternatingly produce a pressure reduction and a pressure increase in the housing, wherein within said housing a support means is arranged to take the user's body weight off said legs, and wherein a permanent interval switching between low pressure and increased pressure takes place in said housing within a period of 10 to 90 seconds if a low pressure of 0.02 to 0.05 bar is reached, wherein said work-out device is adapted to generate a treading resistance, said treading resistance being coupled to said interval switching such that the treading resistance increases while said low pressure acts on said user.

21. Apparatus according to claim 1, wherein said work-out device generates a treading resistance being set to 0.8 to 2 watts per kilogram body weight of the person.

22. Apparatus according to claim 21, wherein said treading resistance is decreased if said seat is moved from a low position to a high position within said pressure chamber.

23. Apparatus according to claim 1, wherein said work-out device is actuated by a treading motion of the person's legs, and including a monitoring means for monitoring the treading motion and for interrupting a power supply to said pressure device if said treading motion is interrupted for a predetermined time.

24. Apparatus according to claim 1, wherein said work-out device is actuated by a treading motion of the person's legs, and including a monitoring means and at least one valve, said monitoring means monitoring the treading motion and opening said at least open valve if said treading motion is interrupted for a predetermined time.

25. Apparatus according to claim 1, wherein said work-out device generates a treading resistance, said treading resistance being coupled to said alternating pressure reduction and pressure increase in said housing.

26. The method according to claim 8, comprising the following steps:

generating a continuous change between a pressure below atmosphere and a high pressure above atmosphere, and coupling the change in pressure to the resistance.

27. The method according to claim 26, comprising the step of increasing the resistance when decreasing the pressure.

28. The method of claim 8, comprising the following steps:

having said person use said work-out means by performing a treading motion, monitoring said treading motion, interrupting the pressure decrease if said treading motion is interrupted for a predetermined period of time.

\* \* \* \* \*